United States Patent [19]

Hall et al.

[11] 4,143,426

[45] Mar. 13, 1979

[54] PERMANENTLY ATTACHED ARTIFICIAL LIMB

[75] Inventors: C. William Hall, Boerne; William A. Mallow; Fred O. Hoese, both of San Antonio, all of Tex.

[73] Assignee: The United States of America as represented by the Administrator of Veterans Affairs, Washington, D.C.

[21] Appl. No.: 782,849

[22] Filed: Mar. 30, 1977

[51] Int. Cl.$^2$ ............................ A61F 1/08; A61F 1/24
[52] U.S. Cl. ................................................ 3/6; 3/1.9; 3/1; 128/92 C
[58] Field of Search ...................... 3/1, 1.9, 1.91, 2, 6, 3/30; 128/92 C, 334 R

[56] References Cited

U.S. PATENT DOCUMENTS

| | | | |
|---|---|---|---|
| 3,805,300 | 4/1974 | Tascon-Alonso et al. .................. | 3/1 |
| 3,947,897 | 4/1976 | Owens ..................................... | 3/1.9 |
| 3,971,670 | 7/1976 | Homsy ..................................... | 3/1 X |

OTHER PUBLICATIONS

"A Permanently Attached Artificial Limb" by C.W. Hall et al., Transactions American Society For Artificial Internal Organs, vol. XIII, 1967, pp. 329-331.

Primary Examiner—Ronald L. Frinks
Attorney, Agent, or Firm—Browdy and Neimark

[57] ABSTRACT

A permanently attached artificial limb comprises an endoprosthesis in combination with an artificial tendon attachment. The artificial tendon attachment permits the use of existing skeletal muscles to power external articulating mechanical joints of the endoprosthesis device. The artificial tendon penetrates the skin and provides a strong interface with existing skeletal muscles.

18 Claims, 8 Drawing Figures

U.S. Patent  Mar. 13, 1979  Sheet 1 of 3  4,143,426
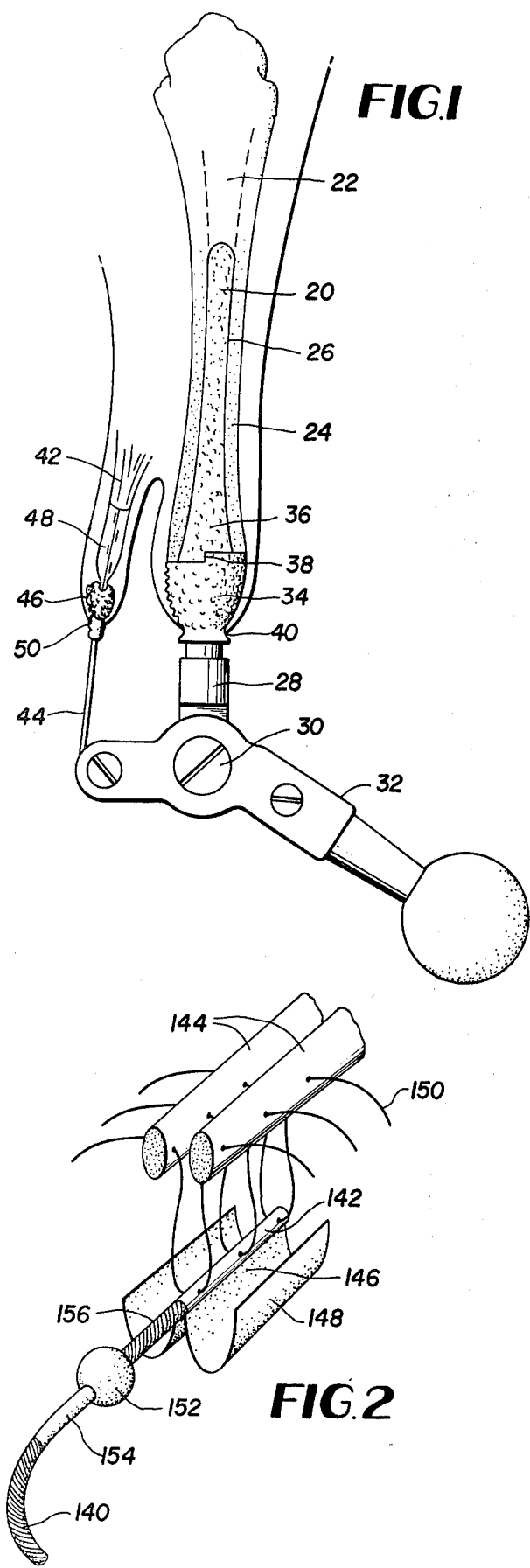
FIG.1
FIG.2
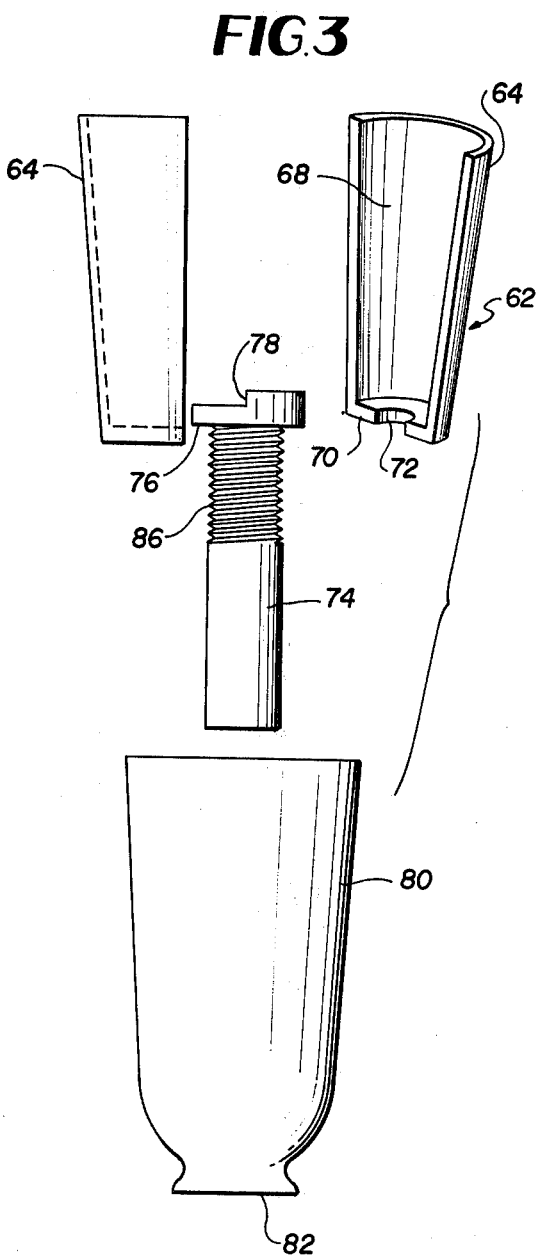
FIG.3

FIG.5
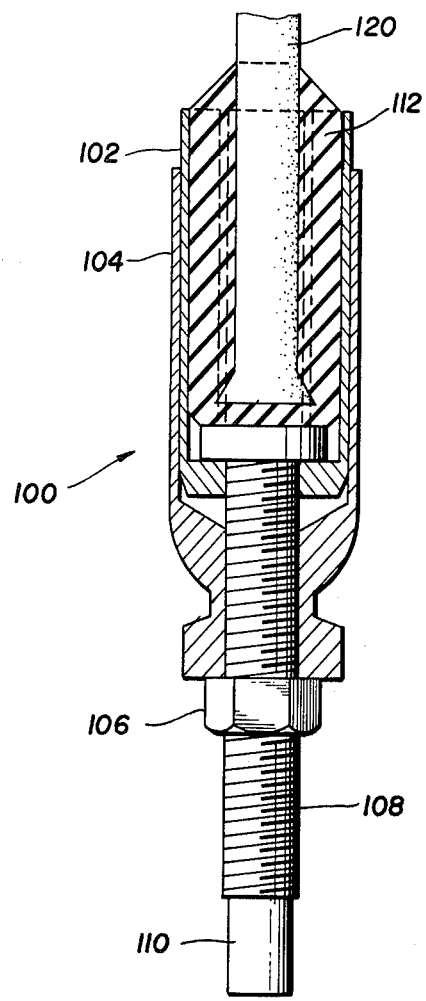
FIG.6
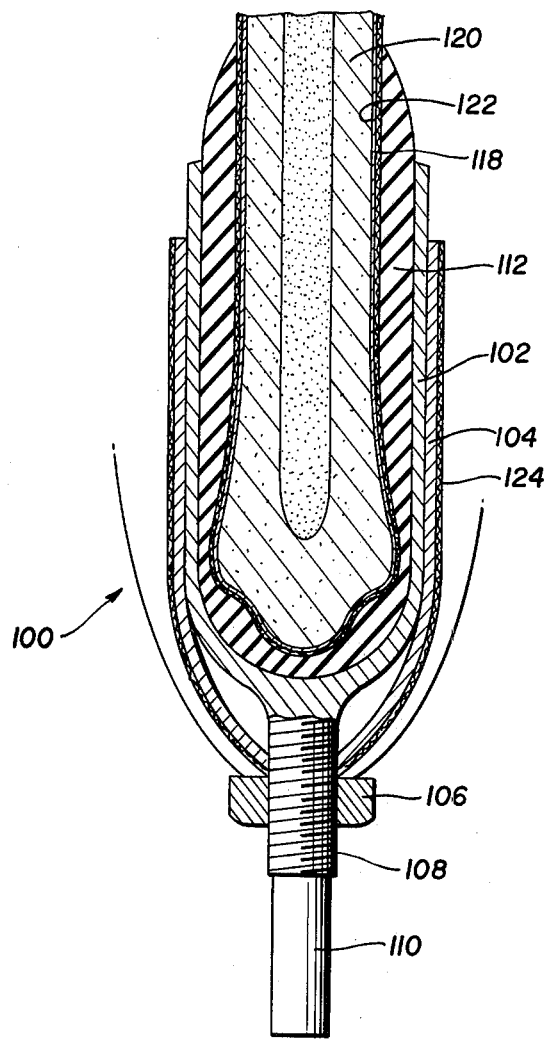
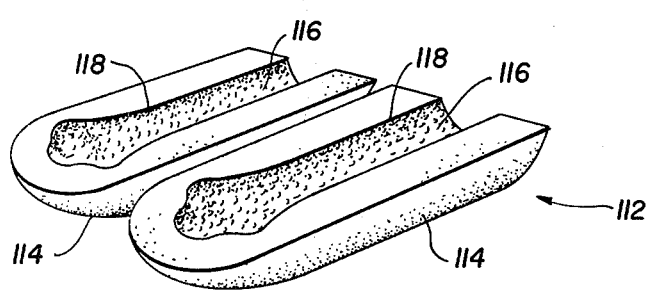
FIG.7

PERMANENTLY ATTACHED ARTIFICIAL LIMB

FIELD OF THE INVENTION

The invention relates to a permanently attached artificial limb and more particularly to the use of an artificial tendon attachment which permits the use of existing skeletal muscles to power external articulating mechanical joints of an endoprosthesis.

BACKGROUND OF THE INVENTION

Prosthetic limbs as presently used are designed for optimum function and esthetic appearance. The art of fabricating prosthetic limbs with natural appearance is quite advanced, but the function of the limbs has been dependent upon secondary muscle control rather than primary muscle control except in kineplastic procedures. The concept of a percutaneous skeletal extension being used as a permanent functional weight-bearing protrusion or extension from the bone is not new but a major problem to the realization of such a permanent endoprosthetic device has been the attainment of a permanent intact skin-prosthetic interface.

The development of a protruding skeletal extension suitable for attaching a functional artificial limb has progressed through a number of design changes. Each change has been an attempt to solve identified and defined problems. A review of past mistakes and successes led to the establishment of the following criteria for future development of this type of device:

(1) The device must be a skeletal extension penetrating the skin in such a manner that the normal loads are transmitted directly to the skeletal system and not through thick layers of intervening soft tissues.

(2) These loads must be distributed in such a manner so as not to damage the prosthesis, the bone to which it is attached, or any interfacial tissue ingrowth.

(3) Both gross and microanatomical limitations must be kept in mind so that the device neither restricts the circulation nor otherwise impedes tissue healing.

(4) In its final application, the skeletal extension must be a functional unit that permits freedom of motion and causes no pain.

(5) The design should preferably permit minor adjustments to be made externally rather than require secondary operative procedures.

(6) The device must have a surface suitable for tissue adhesion and/or ingrowth both at the bone interface and at the skin interface. The skin interface must prohibit the development of a sinus tract and inhibit bacterial invasion.

(7) All materials used in fabrication must be compatible with interfacing tissues, must become functional for the purpose intended, and must not cause adverse systemic reactions.

(8) The total end product must be readily sterilizable, using routine hospital procedures, prior to implantation.

(9) The device should be designed to permit easy application under standard operating room conditions.

(10) Ultimately, the design should permit use of existing skeletal muscles to power external articulating mechanical joints. This, of course, demands development of an artificial tendon that will provide a strong tenacious interface with the musculotendinous portion of the existing skeletal muscles, penetrate the skin without allowing any entrance for bacterial invasion, and transmit the muscle's power to the load in an efficient manner.

The integument or skin is the body's first line of defense against microbial invasion. In the presence of implanted foreign material, particularly a protruding skeletal extension attached directly to the bone, it becomes even more important to maintain the integrity of the skin. Once the bacterial barrier of the integument has been broken, infection occurs and leads to the rejection of the implanted foreign material.

Our experience with skin interfacing has been reported in several articles. Metals, plastics, and ceramics have been tried, utilizing a variety of surface topography, including solids, textiles and foams. Some investigators have found carbon a useful skin interfacing material. No material has yet been found that is considered to be ideal, although Dacron, i.e. polyethylene terephthalate, and nylon velour fabrics bonded to a solid surface so as to form impervious laminates have thus far offered the most suitable solution.

Another problem is bone interfacing. Certain types of porous ceramics and sintered metals allow new bone ingrowth into the porous structure of the material.* It is also possible to have adhesion of bone to a solid non-porous surface. However, bone interfacing in general and surface ingrowth in particular are much more difficult and often disturbed when presented with a dynamic load such as would be applied constantly to a functional endoprosthesis device.

* See, for example, U.S. Pat. Nos. 3,808,606 to Tronzo and 3,855,638 to Pilliar.

Primary muscle extension or a functional attachment under the control of the primary muscles is greatly desired in a prosthetic limb.

Artificial tendons are known, but they have generally been attached by means of sutures or the like. The simple use of sutures has consistently led to failure due to stresses concentrated on the sutures. Either the suture breaks or it tears through the tissue. However, some alternatives have been suggested as noted by the following patents.

U.S. Pat. No. 3,745,590 to Stubstad shows an articulating prosthesis for a body joint which requires unrestricted orbiting motion with a flexible ligamentous element attached. The ligamentous element is affixed to the prosthesis device and adapted to be tied or otherwise affixed to an adjacent tendon, ligament or bone. The combination prosthesis/ligament is contained entirely within the human body. No part extends beyond the skin.

The Treace U.S. Pat. No. 3,953,896 discloses a prosthetic ligament for replacing a natural ligament flexibly connecting two skeletal members together. U.S. Pat. No. 3,973,277 to Semple et al discloses a tendon prosthesis and means to attach a tendon, either natural or artificial, to bone.

Stoy et al, U.S. Pat. No. 3,987,497, discloses another tendon prosthesis, and a suitable material for the core of the artificial tendon which will give it satisfactory physical properties such as tensile strength and elasticity. The Treace U.S. Pat. No. 3,988,783 shows a prosthetic ligament for replacing one of the collateral ligaments of the knee joint. It includes a bridge member and connector elements at the ends of the bridge member to connect to the bones of the leg.

The Homsy U.S. Pat. No. 3,992,725 relates to implantable material and appliances and methods of stabilizing body implants. One particular human implantation use of the growth-promoting material is as a prosthetic tendon. The growth-promoting material is bonded to the ends of the artificial tendon so that the tendon can be attached to the muscle at one end and to the bone at the other end.

In our earlier attempts, we used nylon and Dacron velour bonded to artificial tendon, the velour serving to attach the tendon to the musculotendinous portion by providing a site for tissue ingrowth. When such technique proved unsatisfactory, an impervious layer was bonded to the back of the velour to improve performance.

To attach an artificial tendon to a musculotendinous portion of a skeletal muscle may not per se pose difficult problems but to form an interface that will maintain the union under the repeated stresses of dynamic loading is a major problem. Furthermore, to bring the tendon out through the skin for external loading presents substantial additional problems. As with the skeletal extension itself, the integrity of the integument must be maintained in a manner that prohibits bacterial invasion.

One form of skeletal extension utilized experimentally has been an intramedullary rod held in position by friction.* But problems arose because the intramedullary rod interrupted the bone's main circulatory supply via the nutrient artery within the medullary canal. Thus, this device proved unsatisfactory as a skeletal extension.

* A Permanently Attached Artificial Limb, Hall et al, *Trans. Amer. Soc. Artif. Int. Organs,* 1967, Vol. XIII, pp. 329-331.

SUMMARY OF THE INVENTION

It is accordingly, an object of the present invention to overcome defects in the prior art, such as indicated above.

It is another object to provide for improved prosthetic devices.

It is a further object of the invention to provide an artificial body member having a skeletal extension penetrating the skin in such a manner that the normal loads are transmitted directly to the skeletal system and not through the layers of intervening soft tissues.

It is yet another object of the invention to distribute loads in a prosthetic device in such a manner so as not to damage the prosthesis, the bone to which it is attached, or any interfacial tissue ingrowth.

It is another object of the invention to provide such a device which neither restricts the circulation nor otherwise impedes tissue healing.

It is also an object to provide a skeletal extension serving as a functional unit, permitting freedom of motion and causing no pain.

It is another object of the invention to provide a permanently skeletal attached prothesis having means whereby minor adjustments can be made externally rather than requiring secondary surgical procedures.

It is a further object of the invention to provide such a device having a surface suitable for tissue adhesion and/or ingrowth both at the bone interface and at the skin interface.

It is another object of the invention to provide such a device having a skin interface which prohibits the development of a sinus tract and inhibits bacterial invasion.

It is an object of the invention to permit use of existing skeletal muscles to power external articulating mechanical joints.

It is another object of the invention to provide an artificial tendon with a strong tenaceous interface with the musculotendinous portion of the existing skeletal muscles.

It is a further object of the invention to provide an artificial tendon which will penetrate the skin without allowing any entrance for bacterial invasion.

It is another object of the invention to provide an artificial tendon that will transmit the muscle's power to the load in an efficient manner.

An artificial tendon is attached to the musculotendinous portion of the muscle (or the tendon stump) by using an interfacing material which will distribute the forces over a wide area, additionally the tendon is passed through the skin using a skin interfacing which prevents infection and also tearing of the skin. The artificial tendon can be used as a single implant to take the place of a destroyed tendon.

Such an artificial tendon can be used in combination with an endoprosthesis to couple existing skeletal muscles to an external articulating device.

BRIEF DESCRIPTION OF THE DRAWINGS

These and other objectives, features and advantages of the invention will become more readily apparent from the following detailed description of the preferred embodiments taken with reference to the drawings in which:

FIG. 1 is a schematic view of a permanently attached articulating skeletal extension with an artificial tendon attachment in the form of an intramedullary rod adapted for the leg of a goat and connected to the Achilles tendon.

FIG. 2 shows a method of attaching the artificial tendon to the Achilles tendon using a velour sheath and providing a skin interface using a velour covered silastic ball.

FIG. 3 is an exploded, partly perspective view of a supracortical endoprosthesis, showing how the split collet, extension rod, and forcing cone fit together.

FIG. 5 is a supraperiosteal endoprosthesis.

FIG. 6 is a supraperiosteal endoprosthesis, as in FIG. 4, partly in section, showing the soft tissue interface.

FIG. 7 shows a pre-cast velour lined elastomer for use in the supraperiosteal endoprosthesis of FIG. 5.

DESCRIPTION OF THE PREFERRED EMBODIMENTS

Figure 4A:
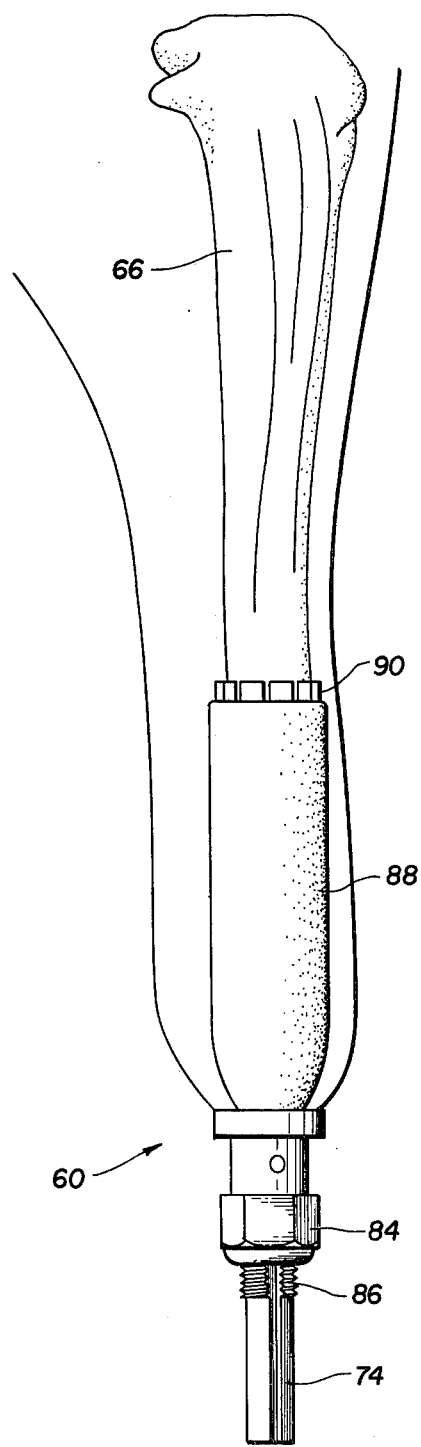
FIGS. 4A and B show a supracortical endoprosthesis attached to the leg.

A permanently attached skeletal extension with an artificial tendon attachment is shown in FIG. 1 in the embodiment of an artificial foot for a goat. An intramedullary rod 20 is driven into the medullary canal 22 of the tibia 24, the surface of the intramedullary rod 20 being coated with a layer 26 of porous polymethyl methacrylate hereinafter designated as PPMM. The intramedullary rod 20 has an external extension 28 with an external articulating joint 30 on which is pivotably mounted an articulating member 32. A plastic pedestal 34 is molded to the intramedullary rod 20 to support the tibial stump 36. A mortise joint 38 between the tibial stump 36 and the pedestal 34 is provided to keep the intramedullary rod 20 from rotating. The pedestal 34 is covered with velour fabric, e.g. of nylon or Dacron, to allow skin attachment at the skin interface 40.

The external articulating member 32 is attached to the Achilles tendon 42 by an artificial tendon 44. The artificial tendon 44 is attached to a velour covered silicone (Silastic) ball 46 which in turn is connected to a velour sheath 48 which is attached to the stub of the Achilles tendon 42. The velour covered Silastic ball 46 provides a large surface area at the skin interface 50 to maintain the integrity of this skin interface under applied stress.

The musculotendinous and skin interfaces which have been briefly described with respect to FIG. 1 are now amplified with reference to FIG. 2. The novel means of attachment of the artificial tendon to the musculotendinous portion of a skeletal muscle allow the use of an artificial tendon by itself as a prosthetic tendon or in combination with an external articulating skeletal extension. The artificial tendon 140 may be a seine cord of nylon. A velour laminate is bonded to the end 142 of the artificial tendon 140. The end 142 is the end of the artificial tendon 140 which will be attached to the skeletal muscle or tendon 144 which in FIG. 2 is shown as the bipenniform Achilles tendon. To the end 142 is also attached or bonded a velour strip 146 of, for example, dimensions of 4 cm by 3 cm, which has an impervious backing 148, e.g. of Silastic, bonded to the back of the velour. The artificial tendon 140 is initially surgically attached to, e.g. the bipenniform Achilles tendon 144 by sutures 150.

The velour surface of the strip 146 and to a lesser degree the velour laminated end 142 provide a mechanism for attaining a strong attachment to the muscle or tendon 144 by allowing a wide surface area for tissue ingrowth. The bonded Silastic surface 148 on the back of the velour serves to isolate the velour from tissue ingrowth except at the interface between the tendon and the velour; otherwise, tissue would grow to both sides of the velour strip 146 causing the artificial tendon 140 to become immobilized. The segment 156 of the artificial tendon 140 which is adjacent to the end 142 is made of an impervious material, like the rest of the tendon 140, so that it will not support tissue ingrowth and become immobilized. The surface area for tissue ingrowth at the interface between the tendon 144 and the velour strip 146, preferably made of nylon or Dacron velour, produces a strong musculotendinous interface even under the repeated stresses of dynamic loading.

When the artificial tendon 140 is used in combination with an articulating skeletal extension as shown in FIG. 1, a strong and bacterial-impervious skin interface must be provided, as well as a strong musculotendinous interface, in order to prevent bacterial invasion. This is best shown in FIG. 2 where a large velour surface for sealing the wound is used. Thus, a velour covered ball 152 of inert material, preferably Silastic, is formed integral with or attached to the artificial tendon 140 at a location where the artificial tendon will pass through the skin. The portion 154 of the artificial tendon 140 adjacent to the ball 152 is also covered with velour. The large velour surface area of the ball 152 and artificial tendon portion 154 provide a strong skin interface under the stresses of external loading. A tunnel of skin about the interface serves as a bellows to take up the slack necessary for tendon contraction and extension, i.e. axial movement, without the tendon sliding through and breaking the skin. The narrow artificial tendon 140 penetrates the skin, but the velour covered ball 152, into which the skin grows, causes the skin to move with the tendon rather than cause the tendon to break therethrough. The ball 152 may be about 1 centimeter in diameter.

A supracortical endoprosthesis 60 as best shown in FIGS. 3 and 4A provides a direct bone interface of the skeletal extension to the bone. The split collet, shown in FIG. 3, comprises two halves 64 which grip the prepared end of the tibial diaphysis 66. The preferred embodiment of the split collet 62 is a tapered configuration, although a cylindrical configuration is also possible. The interior surface 68 of the split collet 62 is coated with an interfacing material such as PPMM, bioglass, orthoplate carbon or sintered porous stainless steel to support osseous ingrowth. The end of the tibial diaphysis 66 is prepared in a tapered shape by means of a pencil sharpener-like device so that the split collet 62 will fit tightly. The base 70 of the split collet halves 64 has a semi-circular hole 72 cut out so that when the two halves 64 are joined the extension rod 74 will pass through the hole in the base 70. The extension rod 74 is held within the split collet 62 by the extension rod cap 76.

The mortised top surface 78 of the extension rod cap 76 abuts the distal end of the bone which is similarly mortised to correspond to the surface 78 to eliminate rotation by the extension rod 74. Pressure is applied to the split collet 62 to grip the bone 66 and to hold the extension rod 74 by the forcing cone 80 which slips over the split collet 62. The extension rod 74 extends through the axial hole 82 in the forcing cone 80. The forcing cone 80 is driven over the split collet 62 by means of the jam nut 84 which is tightened along the threaded portion 86 of the extension rod 74. In the preferred embodiment, as illustrated in FIG. 4, the jam nut 84 is external to the body so that adjustments can be made without further surgical procedures. The forcing cone 80 is coated with a bonded layer 88 of nylon velour fabric to support skin attachment.

Figure 4B:
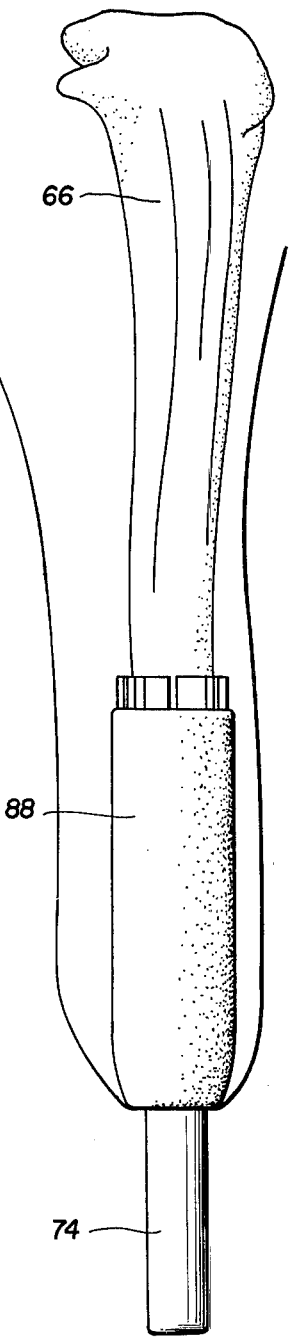

The preferred embodiment of the split collet 62 comprising two halves 64 is shown in FIG. 3. Another embodiment shown in FIG. 4A, comprises a three-part collet having longitudinal cuts to form flexible tines 90 in each collet to allow space for vascular growth and better distribution of forces. An earlier embodiment which did not permit external adjustment is shown in FIG. 4B.

A supraperiosteal endoprosthesis 100 as best shown in FIGS. 5 and 6 provides a soft tissue interface of the artificial limb with the periosteum or soft tissue which covers all bones. Similar to the supracortical endoprosthesis already described, the supraperiosteal endoprosthesis 100 comprises a bipart collet 102 and the forcing cone 104 driven over the collet 102 by means of a jam nut 106 which is tightened on a threaded portion 108 of the extension rod 110. The collet 102 is filled with a precast elastomer 112 as shown in FIG. 7. The precast elastomer 112 is made of two halves 114 and is preferably made of Silastic. The two halves 114 contain a canal 116 and have a velour lining 118. The precast elastomer 112 is held around the tibia 120 or other bone to which the skeletal extension is attached. With the bone fitting in the canal 116 formed in the elastomer 112, the velour lining 118 of the canal 116 contacts the periosteum 122 which covers the bone forming a soft tissue interface between the skeletal extension and the periosteum of the bone. Pressure is applied to the bone via the elastomer 112 by tightening the jam nut 106 to drive the forcing cone 104 onto the collet 102 which forms a swaging socket holding the elastomer 112.

In the preferred embodiment the collet 102 and forcing cone have parallel sides, but they can also be constructed with tapered sides as the supracortical endoprosthesis. The forcing cone 104 has a nylon velour coating 124 to provide a suitable skin interface as in the supracortical endoprosthesis.

Experimental results have been obtained for 51 goats using the four skeletal extension embodiments. The first 27 had an intramedullary rod implanted, with six of the 27 having in combination with the skeletal extension an exteriorized artifical tendon implanted to the Achilles tendon. One goat had only the Achilles tendon replaced by an arificial tendon and this procedure has proven permanently successful. Three embodiments of the supracortical endoprosthesis have been used as implants on 24 additional goats. The first supracortical embodiment did not permit external adjustment and therefore as a result of osteoclysis of the bone, subsequent loosening of the collets occurred. The second supracortical embodiment allowed external readjustment of the collet's compression post-operatively through the tightening of the external jam nut. The third embodiment of the supracortical endoprosthesis used a three-part collet having longitudinal cuts to form flexible tines in each collet thus allowing space for vascular growth between each tine and better distribution of forces.

Although preferred embodiments of the present invention have been described herein with reference to the accompanying drawings, it is to be understood that the invention is not limited to those precise embodiments and that various changes and modifications may be made by one skilled in the art without departing from the scope of this invention.

What is claimed is:

1. An artificial tendon for forming a strong musculotendinous interface with a skeletal muscle, comprising:
   a cord of high break strength forming the body of the artificial tendon;
   tissue ingrowth means to promote musculotendinous attachment, having an interfacing surface with a relatively large surface area bonded to one end of said cord, said tissue ingrowth means being wrappable about the end of a skeletal muscle or tendon to form a large interface; and
   a tissue ingrowth impervious backing bonded to the back non-interfacing surface of said tissue ingrowth means;
   whereby a strong interface is provided for tissue ingrowth from the skeletal muscle to the large surface area of said tissue ingrowth means while said impervious backing prevents tissue ingrowth on the non-interfacing surface and prevents the artificial tendon from being thereby immobilized, so that the artificial tendon remains securely attached to the skeletal muscle while being slidable in the body with the contraction or extension of the skeletal muscle.

2. An artificial tendon as claimed in claim 1, wherein said tissue ingrowth means is a velour strip.

3. The artificial tendon of claim 2, wherein said velour strip is selected from the group consisting of nylon velour and velour fabric of fibers of polyethylene terephthalate.

4. The artificial tendon of claim 2, wherein said velour strip has dimensions of about 4 cm × 3 cm.

5. An artificial tendon as claimed in claim 1, wherein said impervious backing is a layer of silicone.

6. An artificial tendon as claimed in claim 1, further including skin interfacing means to provide a tissue ingrowth surface of large surface area at the skin interface, whereby when the artificial tendon is used to attach an external articulating joint of an endoprosthesis to a skeletal muscle, the artificial tendon penetrates through the skin and the skin interfacing means provides a strong interface under external dynamic loading of the artificial tendon.

7. An artificial tendon as claimed in claim 6, wherein said skin interfacing means comprises a velour covered silicone ball formed in said cord near the end to which said tissue ingrowth means are attached, whereby said ball provides a large tissue ingrowth surface at the skin interface.

8. The artificial tendon of claim 7, wherein said ball is about 1 cm in diameter.

9. An artificial limb adapted to become permanently attached, comprising:
   an endoprosthesis with an external articulating joint; and
   an artificial tendon adapted to connect said external articulating joint to a skeletal muscle with said tendon passing through the skin, said artificial tendon comprising skin interfacing means to provide a tissue ingrowth surface of large surface area at the skin interface, and tissue interfacing means for musculotendenous attachment including a large surface area wrappable about the end of a skeletal muscle or tendon to form a large interface.

10. An artificial limb adapted to become permanently attached, comprising:
    a supracortical endoprosthesis with an external articulating joint; and
    an artificial tendon adapted to connect said external articulating joint to a skeletal muscle with said tendon passing through the skin, said artificial tendon comprising skin interfacing means to provide a tissue ingrowth surface of large surface area at the skin interface.

11. An artificial limb as claimed in claim 10, wherein said supracortical endoprosthesis comprises:
    a collet to grip the distal end of the bone;
    a forcing cone fitting over said collet; and
    an external jam nut which can be tightened to drive said forcing cone over said collet.

12. An artificial limb as claimed in claim 11, wherein the inner surface of said collet is coated with a material conducive to bone ingrowth, whereby a direct bone interface is achieved.

13. An artificial limb as claimed in claim 11, wherein said collet is tapered.

14. An artificial limb as claimed in claim 11, wherein said collet is a split collet.

15. An artificial limb as claimed in claim 11, wherein the outer surface of said forcing cone is coated with a bonded layer of nylon velour to provide tissue ingrowth at the skin interface.

16. An artificial limb adapted to become permanently attached, comprising:
    a supraperiosteal endoprosthesis with an external articulating joint; and
    an artificial tendon adapted to connect said external articulating joint to a skeletal muscle with said tendon passing through the skin, said artificial tendon comprising skin interfacing means to provide a tissue ingrowth surface of large surface area at the skin interface.

17. An artificial limb as claimed in claim 16, wherein said supraperiosteal endoprosthesis comprises:
a collet;
a forcing cone fitting over said collet;
an external jam nut which can be tightened to drive said forcing cone over said collet;
a precast elastomer held within said collet, said precast elastomer having a channel to grip the bone; and
a velour lining on said channel of said precast elastomer whereby said precast elastomer with said velour lining is pressed against the bone by driving said forcing cone over said collet, whereby a soft tissue interface is achieved with the periosteum covering the bone.

18. An artificial limb is claimed in claim 17, wherein said collet and said forcing cone have parallel sides.

* * * * *